United States Patent
Dargis et al.

(10) Patent No.: US 11,446,118 B2
(45) Date of Patent: Sep. 20, 2022

(54) SYSTEMS AND METHODS FOR INTRAORAL DEVICE QUALITY CONTROL

(71) Applicant: SDC U.S. SmilePay SPV, Nashville, TN (US)

(72) Inventors: John Dargis, Nashville, TN (US); Josh Long, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 16/905,154

(22) Filed: Jun. 18, 2020

(65) Prior Publication Data

US 2021/0045845 A1 Feb. 18, 2021

Related U.S. Application Data

(63) Continuation of application No. 16/541,479, filed on Aug. 15, 2019, now Pat. No. 10,687,916.

(51) Int. Cl.
| | |
|---|---|
| *A61C 7/08* | (2006.01) |
| *A61C 9/00* | (2006.01) |
| *A61B 6/14* | (2006.01) |
| *A61C 7/00* | (2006.01) |
| *A61B 5/00* | (2006.01) |

(52) U.S. Cl.
CPC .............. *A61C 7/08* (2013.01); *A61B 6/145* (2013.01); *A61C 7/002* (2013.01); *A61C 9/0053* (2013.01); *A61B 5/0088* (2013.01); *A61B 5/682* (2013.01)

(58) Field of Classification Search
CPC ....... A61B 5/682; A61B 5/0088; A61B 6/145; A61C 9/0053; A61C 7/002; A61C 7/08
See application file for complete search history.

(56) References Cited

U.S. PATENT DOCUMENTS

| | | | | |
|---|---|---|---|---|
| 6,739,869 | B1 * | 5/2004 | Taub | A61C 7/00 433/24 |
| 7,442,041 | B2 * | 10/2008 | Imgrund | A61C 9/0053 433/213 |
| 8,684,729 | B2 * | 4/2014 | Wen | A61C 3/00 433/24 |
| 10,258,439 | B1 | 4/2019 | Kitching et al. | |
| 10,466,676 | B1 * | 11/2019 | Do | G05B 19/402 |
| 10,482,192 | B1 * | 11/2019 | Long | A61C 7/002 |
| 10,687,916 | B1 * | 6/2020 | Dargis | A61B 6/14 |
| 10,945,812 | B1 * | 3/2021 | Raslambekov | G06T 17/20 |

(Continued)

FOREIGN PATENT DOCUMENTS

CN    103079494 A  *  5/2013  ............. A61C 13/00

OTHER PUBLICATIONS

"How it Works—Mouth Guard for Grinding Teeth Pro Teeth Guard" Pro Teeth Guard (Jul. 2021).*

(Continued)

*Primary Examiner* — Mia M Thomas
(74) *Attorney, Agent, or Firm* — Foley & Lardner LLP

(57) ABSTRACT

A method for analyzing a quality of a dental aligner includes receiving, by a processor, a digital dental aligner generated based on a fabricated dental aligner. The method also includes analyzing, by the processor, the digital dental aligner to identify a quality characteristic of the fabricated dental aligner. The method also includes flagging, by the processor, the fabricated dental aligner based on the identified quality characteristic.

19 Claims, 6 Drawing Sheets

(56) References Cited

U.S. PATENT DOCUMENTS

| | | | |
|---|---|---|---|
| 10,970,839 B2* | 4/2021 | Parpara | A61C 7/002 |
| 10,980,621 B2* | 4/2021 | Lancelle | G06T 19/20 |
| 11,007,042 B2* | 5/2021 | Long | B29C 64/20 |
| 11,083,552 B2* | 8/2021 | Lancelle | A61C 9/0053 |
| 11,109,947 B2* | 9/2021 | Adamson | A61B 1/00045 |
| 11,288,410 B2* | 3/2022 | Long | A61C 7/002 |
| 2001/0038705 A1* | 11/2001 | Rubbert | A61C 7/00 382/128 |
| 2004/0209218 A1 | 10/2004 | Chishti et al. | |
| 2006/0063135 A1* | 3/2006 | Mehl | A61C 9/0053 433/223 |
| 2008/0118886 A1 | 5/2008 | Liang et al. | |
| 2008/0187887 A1 | 8/2008 | Lu et al. | |
| 2008/0306724 A1 | 12/2008 | Kitching et al. | |
| 2009/0191503 A1 | 7/2009 | Matov et al. | |
| 2013/0095446 A1* | 4/2013 | Andreiko | A61C 7/08 433/6 |
| 2013/0122448 A1* | 5/2013 | Kitching | A61C 7/002 433/24 |
| 2013/0275107 A1* | 10/2013 | Alpern | A61C 9/0046 382/128 |
| 2013/0308846 A1* | 11/2013 | Chen | A61B 6/14 382/131 |
| 2014/0080093 A1* | 3/2014 | Rubbert | A61B 6/14 433/175 |
| 2014/0315153 A1 | 10/2014 | Kitching et al. | |
| 2015/0132707 A1 | 5/2015 | Huang et al. | |
| 2016/0074138 A1 | 3/2016 | Kitching et al. | |
| 2016/0220200 A1 | 8/2016 | Sandholm et al. | |
| 2016/0242870 A1 | 8/2016 | Matov et al. | |
| 2016/0242871 A1 | 8/2016 | Morton et al. | |
| 2017/0100207 A1* | 4/2017 | Wen | A61C 7/08 |
| 2017/0100211 A1* | 4/2017 | Wen | A61C 7/002 |
| 2017/0231721 A1* | 8/2017 | Akeel | A61C 7/14 433/24 |
| 2017/0304023 A1 | 10/2017 | Tsai et al. | |
| 2018/0055600 A1 | 3/2018 | Matov et al. | |
| 2018/0110589 A1* | 4/2018 | Gao | A61C 7/002 |
| 2018/0153649 A1* | 6/2018 | Wu | G16H 40/67 |
| 2018/0177570 A1 | 6/2018 | Alauddin et al. | |
| 2018/0303581 A1* | 10/2018 | Martz | A61C 7/002 |
| 2018/0304497 A1 | 10/2018 | Kitching et al. | |
| 2018/0324577 A1* | 11/2018 | Faccin | H04W 76/27 |
| 2018/0333226 A1 | 11/2018 | Tsai et al. | |
| 2019/0008612 A1 | 1/2019 | Kitching et al. | |
| 2019/0026598 A1 | 1/2019 | Salah et al. | |
| 2019/0029522 A1 | 1/2019 | Sato et al. | |
| 2019/0046298 A1* | 2/2019 | Cinader, Jr. | A61C 7/20 |
| 2019/0102880 A1 | 4/2019 | Parpara et al. | |
| 2019/0164353 A1 | 5/2019 | Yancey et al. | |
| 2019/0201296 A1* | 7/2019 | Wang | A61K 6/90 |
| 2019/0231477 A1 | 8/2019 | Shanjani et al. | |
| 2020/0015937 A1* | 1/2020 | Stewart | B32B 25/08 |
| 2020/0100871 A1* | 4/2020 | Wang | G06F 30/27 |
| 2020/0146776 A1* | 5/2020 | Matov | A61C 7/002 |
| 2020/0242765 A1* | 7/2020 | Parpara | G06T 7/0014 |
| 2020/0383758 A1* | 12/2020 | Yancey | A61C 9/0053 |
| 2021/0137653 A1* | 5/2021 | Saphier | G06T 19/20 |
| 2021/0196430 A1* | 7/2021 | Wilson | G06F 30/30 |
| 2021/0353386 A1* | 11/2021 | Raby | A61C 7/08 |
| 2022/0022828 A1* | 1/2022 | Schulze-Ganzlin | A61B 6/501 |

OTHER PUBLICATIONS

Dedum et al. "Digital Michigan splint—from intraoral scanning to plasterless manufacturing"—International Journal of Computerized Dentistry 2016;19(1):63-76.*

Hao et al. "Toward Clinically Applicable 3-Dimensional Tooth Segmentation via Deep Learning"; Journal of Dental Research 1-8 International Association for Dental Research and American Association for Dental.*

Ronald E. Goldstein's Esthetics in Dentistry—2018.* www.itero.com—Our products page.* www.digitaldental.com—About us page.*

AAO Consumer Alert—Special Attention page.*

Papagiannis, A. "Shape variation and covariation of upper and lower dental arches of an orthodontic population" European Journal of Orthodontics, vol. 38, Issue 2, Apr. 2016, pp. 202-211, Apr. 3, 2015.*

International Search Report and Written Opinion on International Application No. PCT/US2020/046194, dated Nov. 2, 2020, 11 pages.

* cited by examiner

SYSTEMS AND METHODS FOR INTRAORAL DEVICE QUALITY CONTROL

CROSS-REFERENCE TO RELATED APPLICATIONS

This application is a continuation of U.S. patent application Ser. No. 16/541,479, filed Aug. 15, 2019, which is incorporated herein by reference in its entirety.

TECHNICAL FIELD

The present disclosure relates generally to analyzing fabricated intraoral devices, and more particularly, to systems and methods for inspecting the quality of fabricated intraoral devices, such as dental aligners.

BACKGROUND

Intraoral devices may be worn by a patient receiving orthodontic treatment. Some intraoral devices, such as dental aligners, retainers, and dentures, may be fabricated by thermoforming a material to a dental mold. After thermoforming the material to the dental mold, the formed material is cut from the dental mold, and visually inspected by a technician for quality assurance purposes. However, such manual visual inspections are time consuming, and it may be difficult to determine through manual visual inspections whether the fabricated intraoral device matches the dental mold or whether there are other issues with the fabricated intraoral device.

SUMMARY

According to an example embodiment, a method for analyzing a quality of a dental aligner includes receiving, by a processor, a digital dental aligner generated based on a fabricated dental aligner. The method also includes analyzing, by the processor, the digital dental aligner to identify a quality characteristic of the fabricated dental aligner. In response to determining, that the quality characteristic is anomalous, the method includes causing, by the processor, a fabrication computing system to fabricate a replacement dental aligner.

According to another example embodiment, a system for analyzing a quality of a dental aligner includes a processor and memory coupled to the processor and storing instructions that, when executed by the processor, cause the processor to receive, a digital dental aligner generated based on a fabricated dental aligner, analyze the digital dental aligner to identify a quality characteristic of the fabricated dental aligner, determine that the quality characteristic is anomalous, and cause a fabrication computing system to fabricate a replacement dental aligner.

According to another example embodiment, a quality control system includes an imaging system, a processor, and a memory coupled to the processor and storing instructions. The imaging system is configured to enhance a quality characteristic of a fabricated dental aligner, capture an image of the quality characteristic, and generate a digital dental aligner including the quality characteristic of the fabricated dental aligner based on the captured image. When the instructions are executed by the process, the instructions cause the processor to analyze the quality characteristic of the digital dental aligner, determine that the quality characteristic is anomalous, and cause a replacement dental aligner to be fabricated.

BRIEF DESCRIPTION OF THE DRAWINGS

The foregoing and other features of the various embodiments of the methods and apparatuses described herein will become more apparent from the following detailed description and the accompanying drawings in which.

DETAILED DESCRIPTION

Figure 1:
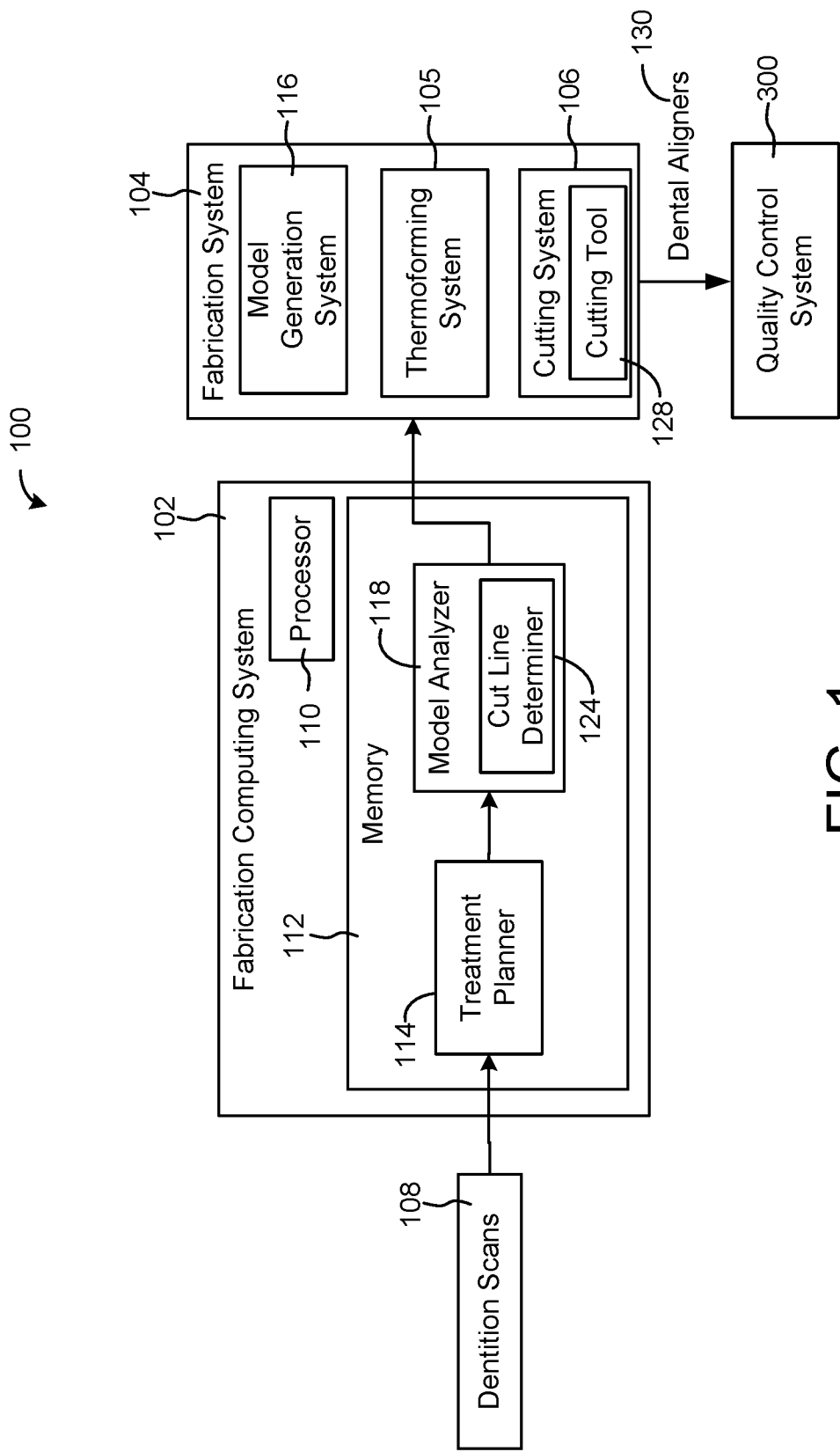
FIG. 1 is a block diagram showing a system for fabricating dental aligners, according to an illustrative embodiment.

Before turning to the figures, which illustrate certain example embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, described herein are systems and methods for inspecting the quality of fabricated intraoral devices, such as dental aligners. While this application refers to dental aligners specifically throughout, it will be appreciated that the systems and method disclosed herein could also be used to inspect the quality of other intraoral devices, such as retainers, dentures, and mouth guards, among other devices. According to various embodiments, a computing device analyzes one or more digital representations of the fabricated dental aligner (e.g., a 2D image, a virtual 3D model, or the like) to ensure that the fabricated dental aligner was formed and cut properly from a dental mold to conform to a patient's dentition. For example, in some embodiments, the computing device analyzes various 2D image views of the dental aligner and/or a virtual 3D model of the dental aligner to ensure that various quality characteristics of the fabricated dental aligner are acceptable, such as that the dental aligner was formed and cut to specification and within tolerance (e.g., thickness, dentition coverage, shape, color, clarity, and/or the like) without surface imperfections (e.g., cracks, holes, bubbles, thinned areas, and/or the like).

In some embodiments, a digital representation of the fabricated dental aligner (e.g., a 2D image, a virtual 3D model, or the like) may be compared with a digital representation of the patient's dentition (e.g., a 2D image of a model of the patient's dentition, a digital 3D model of the patient's dentition, or the like) to determine whether shapes and geometries (e.g., contours, features, dental arch, and/or the like) of the dental aligner match the shapes and geometries of the patient's dentition. In some embodiments, the digital representation of the fabricated dental aligner may be compared with a digital cut line file to determine whether the dental aligner was properly trimmed. In various embodiments, the computing device may use various suitable object detection and image comparison algorithms to automatically detect potential abnormalities in the digital representation of the fabricated dental aligner 130, such that the fabricated dental aligner 130 is flagged indicating that the fabricated dental aligner is rejected or is a potential reject. In some embodiments, any flagged dental aligners 130 may be presented for further review (e.g., by a dental technician or other professional). In some embodiments, any flagged dental aligner 130 may cause (e.g., trigger) the fabrication computing system 102 to fabricate a replacement dental aligner 130 for the corresponding patient. For example, in some embodiments, the quality control system 300 may transmit a message to the fabrication computing system 102 and/or the fabrication system 104 to fabricate another dental aligner for the corresponding patient. The replacement dental aligner is fabricated to be the same as the dental aligner that it is replacing but without any defects. In some embodiments, the fabrication process for the replacement dental aligner may be modified to avoid an occurrence of the same defect or another defect. For example, the modification to the fabrication process may be a modification to the dental mold, the material to be thermoformed to the dental mold, a thermoforming process, a marking process, a cutting process, or any other fabrication process. In some embodiments, flagging the dental aligner 130 may include providing, by the quality control system 300, an alert or message (e.g., a visual alert on a display screen, an audible alert, etc.) to a technician indicating that additional review of the dental aligner is recommended or needed.

In some embodiments, the computing device may analyze one or more digital representations of the dental mold (e.g., a 2D image, a virtual 3D model, or the like) used to form the dental aligner to ensure that the same dental mold can be used to form subsequent dental aligners for the patient. For example, in some embodiments, the same dental mold may be used to generate a plurality of dental aligners for the patient for at least one stage (e.g., an initial stage, an intermediate stage, or a final stage) or for each stage of a treatment plan, such that each of the formed dental aligners for the same stage of the treatment plan includes the same shape but with a different thickness or constructed of a different material (e.g., a harder or softer material). In some embodiments, each of the formed dental aligners for the same stage of the treatment plan may be formed and cut from the same dental mold with the same or different cut line. In some embodiments, the computing device may analyze the digital representation of the dental mold to ensure that the dental mold is capable of forming a subsequent dental aligner (e.g., no breaches in the dental mold, no cracks or holes in the wall of the dental mold, no burns or abrasions in the dental mold from a previous cut, and/or the like).

FIG. 1 illustrates an embodiment of a system 100 for fabricating dental aligners, according to some embodiments. The system 100 is shown to include a dental aligner fabrication computing system 102, a fabrication system 104, and a quality control system 300. In some embodiments, the system 100 receives dentition scans 108 (e.g., from a suitable imaging or scanning system), and may fabricate dental aligners 130 from the dentition scans 108. In various embodiments, the dentition scans 108 are three-dimensional representations of a patient's dentition. For example, in some embodiments, the dentition scans 108 may be digital scans of physical dental impressions (e.g., captured by a dental technician, a dentist, the patient using an in-home impression kit, or the like). In other embodiments, the dentition scans 108 may be direct scans of a patient's dentition, for example, as captured by scanning the patient's dentition with a three-dimensional camera. In various embodiments, the dentition scans 108 may be used for fabricating a suitable intraoral device, such as the dental aligner 130 shown in FIG. 2.

In some implementations, the fabrication computing system 102 may be embodied as or include a processing circuit which includes a processor 110 and memory 112. The processor 110 may be a general purpose single-chip or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. The processor 110 may also be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function.

The memory 112 (e.g., memory, memory unit, storage device) may include one or more devices (e.g., RAM, ROM, EPROM, EEPROM, optical disk storage, magnetic disk storage or other magnetic storage devices, flash memory, hard disk storage, or any other medium) for storing data and/or computer code for completing or facilitating the various processes, layers and circuits described in the present disclosure. The memory 112 may be or include volatile memory or non-volatile memory, and may include database components, object code components, script components, or any other type of information structure for supporting the various activities and information structures described in the present disclosure. According to an illustrative embodiment, the memory 112 is communicably connected to the processor 110 via a processing circuit and includes computer code for executing (e.g., by the processing circuit or the processor 110) the processes described herein.

The memory 112 may store various modules or be comprised of a system of circuits. The circuits may include hardware, memory, and/or other components configured or implemented to execute various functions. As shown in FIG. 1, in some embodiments, the memory 112 may include (or store) a treatment planner 114 and a model analyzer 118. The treatment planner 114 may be a circuit designed or implemented to perform various functions corresponding to generating a treatment plan for the patient's dentition (e.g., based on the dentition scans 108). The treatment planner 114 may use the treatment plan to generate one or more plan models (e.g., digital 3D models) based on the treatment plan. The plan models may be three-dimensional representations of the patient's dentition at various intervals (e.g., at the start of the treatment plan and at various intervals throughout the treatment plan). The model analyzer 118 may be configured to analyze the plan models and/or physical models (e.g., dental molds) for fabricating dental aligners 130.

In various embodiments, the treatment planner 114 is configured to produce, generate, assemble, compile, or otherwise create a treatment plan for moving various teeth of a patient's dentition. The treatment plan may be a series of movements for teeth of a patient's dentition from a starting arrangement to an ending arrangement. The treatment plan may be generated by or through use of the treatment planner 114. In some embodiments, a dental technician or professional uses the treatment planner 114 to generate the treatment plan by manipulating individual teeth or groups of teeth shown in the dentition scans 108. For instance, the treatment planner 114 may present the dentition scans 108 to the dental professional, who can then manipulate various teeth within the dentition scans 108.

The treatment planner 114 is configured to generate various stages of the treatment plan to move the teeth from the starting position (e.g., their current position as represented within the dentition scan 108) to a final position selected or provided by the dental professional. In some embodiments, the treatment planner 114 is configured to create the treatment plan without the assistance of a dental professional. For instance, the treatment planner 114 may analyze the dentition scans 108 to align the teeth with a dental arch fitted to the teeth. The treatment planner 114 may then generate various stages of the treatment plan to move the teeth from the starting position to the final position. For example, the treatment planner 114 may generate one or more plan models (e.g., digital 3D models) corresponding to each interval or stage of the treatment plan.

In various examples, the patient is provided a dental aligner 130 to be worn at each stage of the treatment plan for a predetermined duration (e.g., one week, two weeks, one month). The dental aligners 130 are constructed from a material thermoformed (e.g., via a thermoforming system 105) to a physical model (e.g., as generated by the model generation system 116) and are worn in the patient's mouth (e.g., over the patient's teeth). The dental aligners 130 apply a force on at least one of the patient's teeth to move at least one tooth according to the treatment plan.

In some embodiments, at least one stage (e.g., an initial stage) or each stage of the treatment plan includes more than one dental aligner 130 having the same shape but having a different thickness or being constructed of a different material (e.g., a harder or softer material). For example, the treatment plan can specify that the patient wears the softest dental aligner in a first sub-stage, followed by a dental aligner of medium hardness, followed by the hardest dental aligner. In this way, the patient can be acclimated to the dental aligner 130 for the at least one stage or for each of the stages of the treatment plan, by starting with the softer dental aligner and working up to the hardest dental aligner. However, the present disclosure is not limited thereto, and in other embodiments, the patient may be provided with only one dental aligner 130 for each stage or for some stages of the treatment plan.

In some embodiments, the model generation system 116 generates models (e.g., physical models such as dental molds) of the patient's dentition at the various stages of the treatment plan generated by or using the treatment planner 114. The model generator 116 generates a plurality of physical models including an initial model, a final model, and at least one intermediate model. The initial model corresponds to a first stage of the treatment plan. The final model corresponds to a final stage of the treatment plan. Each intermediate model corresponds to an intermediate stage of the treatment plan. In some embodiments, the models generated by the model generator 116 may be physical 3D models of the patient's dentition at the various stages of the treatment plan. For example, in some embodiments, the model generator 116 may include (or be communicably coupled to) a 3D printer to print the physical 3D models. However, the present disclosure is not limited thereto, and in other embodiments, the model generator 116 may generate the physical 3D models using any suitable methods or devices, for example, such as sculpting, pressing, casting, molding, or the like.

In some embodiments, during fabrication of the dental aligners 130, the material thermoformed to the physical model (e.g., via the thermoforming system 105) is trimmed, such that the fabricated dental aligner 130 can fit comfortably within the patient's mouth. In some embodiments, the dental aligners 130 are trimmed to include representations of the patient's teeth and a portion of the patient's gingiva (otherwise referred to as the patient's gums). As described in greater detail below, the model analyzer 118 is configured to determine a cut line for the dental aligners 130 and the model analyzer 118 is configured to control or provide instructions (e.g., a cut line file) to the cutting system 106 to cut the dental aligners 130 along the cut line.

For example, in some embodiments, the model analyzer 118 may be configured to identify the teeth and gingiva (e.g., gum) portions of the model (e.g., plan model or physical model) corresponding to the patient's dentition. For example, the teeth portion of the model corresponds to the teeth of the patient's dentition, and the gingiva portion of the model corresponds to a portion of the gingiva of the patient's dentition. In some embodiments, the model analyzer 118 may be configured to identify the teeth portion within the model using a teeth identification algorithm. The teeth identification algorithm may identify various characteristics within the model which are consistent with the teeth portion, such as surface contours of crowns, separation or gaps in the interproximal region (e.g., the space between the teeth portion), and/or the like. In some embodiments, the model analyzer 118 may be configured to identify the teeth portion within the model, and other portions of the model that are not identified as the teeth portion may be identified as the gingiva portion of the model. In some embodiments, the model analyzer 118 may be configured to generate an object (OBJ) file including each of the teeth and gingiva portions, with each of the teeth and gingiva portions being represented as separate objects within the OBJ file.

In some embodiments, the model analyzer 118 is configured to identify a gingival line for the model (e.g., plan model or physical model) of the patient's dentition. The gingival line may be defined as the juncture or interface between the teeth portion and the gingiva portion of the model. In some embodiments, the model analyzer 118 may be configured to identify the gingival line by identifying a location where the teeth portion and gingiva portion of the model meet. As described above, the model analyzer 118 may be configured to identify a location of the teeth portion within the model, and may identify the location of the gingiva portion as the remaining portions of the model that are not identified as the teeth portion. Similarly, the model analyzer 118 may identify the gingival line based on where the portions of the model identified as the teeth portion meet portions of the model (e.g., the remaining portions) identified as the gingiva portion.

In some embodiments, the model analyzer includes a cut line determiner 124. The cut line determiner 124 is configured to define a cut line for the dental aligner 130. The cut line is a line or path which extends around the model (e.g., dental mold) of the patient's dentition and defines a travel path for a cutting tool 128 of the cutting system 106. The cut line determiner 124 (or a cutting system controller) may control the cutting tool 128 (e.g., various actuators which manipulate or otherwise move the cutting tool 128) to move along the cut line to cut the dental aligner 130 from the model (e.g., from the dental mold). In other embodiments, the cut line determiner 124 (or the cutting system controller)

may move the model (with the dental aligner 130 positioned thereon) relative to the cutting tool 128 such that the cutting tool 128 can cut the dental aligner 130 from the model along the cut line.

Figure 2:
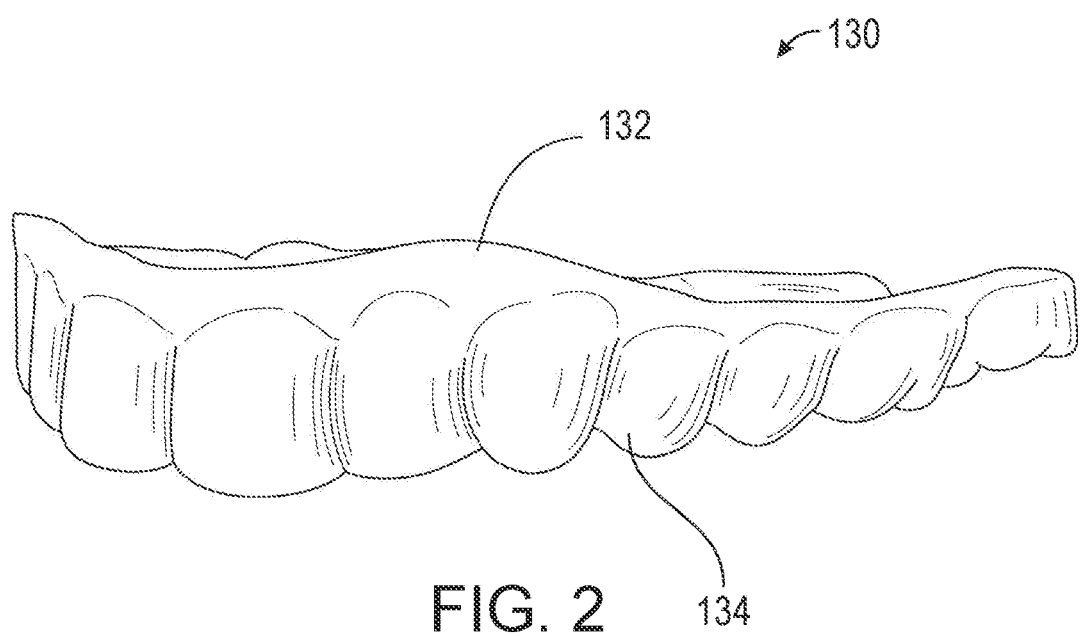
FIG. 2 is an illustration of a dental aligner fabricated using the system of FIG. 1, according to an illustrative embodiment.

Referring to FIG. 2, a dental aligner 130 fabricated using the system 100 of FIG. 1 is shown, according to some embodiments. In some embodiments, the dental aligner 130 is fabricated and cut (e.g., along the cut line) to fit comfortably within the patient's mouth. In some embodiments, the dental aligner 130 is configured to cover the patient's teeth and a portion of the patient's gingiva. Thus, as shown in FIG. 2, the resulting dental aligner 130 includes a gingiva portion 132 corresponding to the portion of the patient's gingiva, and teeth portion 134 corresponding to the patient's teeth.

Referring back to FIG. 1, in some embodiments, after the dental aligner 130 is cut from the model (e.g., dental mold) along the cut line, the quality control system 300 analyzes the fabricated dental aligner 130 to ensure that the dental aligner 130 was formed and cut properly to correctly fit the patient's dentition. For example, in some embodiments, the quality control system 300 may determine whether various quality characteristics of the fabricated dental aligner 130 are abnormal or anomalous, such as, for example, whether there are any cracks, holes, bubbles, areas of opacity, discoloration, or other surface imperfections in the fabricated dental aligner 130. In some embodiments, the quality control system 300 may determine whether various quality characteristics of the fabricated dental aligner 130 are acceptable, for example, whether the fabricated dental aligner 130 matches the contours and features of the patient's dentition correctly, covers the patient's dentition properly, and/or the like. In some embodiments, the quality control system 300 may determine whether the fabricated dental aligner 130 was cut properly from the dental mold. In some embodiments, the quality control system 300 may inspect the dental mold used to form the fabricated dental aligner 130 to determine whether the dental mold is in a suitable condition to form additional dental aligners 130 for the patient. An example embodiment of the quality control system 300 is shown and described in more detail with reference to FIG. 3.

Figure 3:
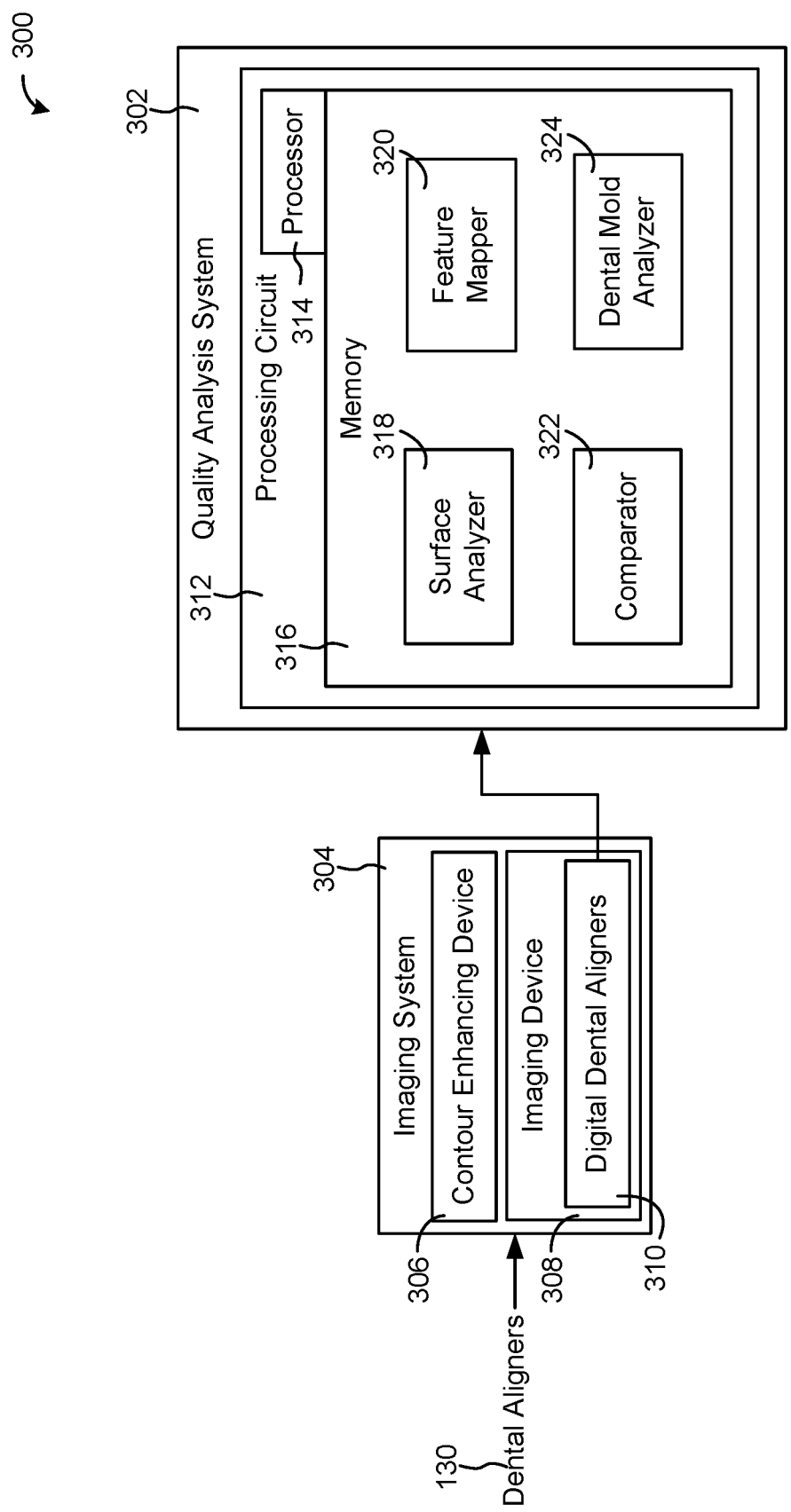
FIG. 3 is a block diagram of a quality control system for analyzing the quality of fabricated dental aligners, according to an illustrative embodiment.

FIG. 3 shows an illustrative quality control system 300 for analyzing fabricated dental aligners, according to some embodiments. In some embodiments, the quality control system 300 may analyze the dental aligners 130 fabricated by the system 100 as described with reference to FIG. 1. While the present disclosure primarily refers to analyzing dental aligners, it is noted that the present disclosure is not limited to only analyzing dental aligners. The present disclosure may be used for analyzing other fabricated intraoral devices such as, but not limited to, mouth guards, retainers, expansion aligners, dentures, and/or the like. Accordingly, it will be appreciated that any system or process disclosed herein can also be used to analyze intraoral devices other than dental aligners.

In use, as described further below, the quality control system 300 acquires or generates one or more digital representations (e.g., a 2D image, a virtual 3D model, or the like) of the fabricated dental aligner 130 (also referred to as a "digital dental aligner"), and analyzes the digital dental aligners 310 to identify any surface imperfections in the corresponding fabricated dental aligner 130. For example, in some embodiments, after the dental aligner 130 is cut from the dental mold, the dental aligner 130 may be scanned (e.g., using a suitable stereoscopic imaging device), and/or one or more photographs of the dental aligner 130 may be captured (e.g., using a camera or other suitable imaging device), such that the digital dental aligner 310 is acquired or generated by the quality control system 300. In some embodiments, the quality control system 300 compares the digital dental aligner 310 with one or more digital representations (e.g., a 2D image, a 3D model, or the like) of the patient's dentition (also referred to as a "digital dentition") to determine whether various quality characteristics (e.g., contours and features) of the dental aligner 130 match (e.g., fit, align with) various contours and features of the patient's dentition. In some embodiments, the digital dental aligner may be compared with a digital cut line file (e.g., as generated by the cut line determiner 124 of FIG. 1) used during fabrication of the dental aligner 130. In some embodiments, the quality control system 300 may acquire or generate one or more digital representations (e.g., a 2D image, a virtual 3D model, or the like) of the dental mold used to form the dental aligner 130, and may analyze the digital representation(s) of the dental mold to determine whether there are any issues with the dental mold. Accordingly, in various embodiments, quality inspections of dental aligners 130 may be automated, while improving inspection quality and time over manual visual inspections by a technician.

As shown in FIG. 3, the quality control system 300 illustratively includes a quality analysis system 302 and an imaging system 304. In other embodiments, the quality control system 300 may include other or additional components and devices commonly found in a server computer or similar computing device, such as, for example, various input/output devices. Before describing the quality control system 300 in more detail, it should be noted that the components of the quality control system 300 can be integrated within a single device or distributed across multiple separate systems or devices. For example, in various embodiments, the quality analysis system 302 may be embodied as any suitable type of computation or computer device capable of performing the functions described herein, including, without limitation, a computer, a server, a workstation, a desktop computer, a laptop computer, a notebook computer, a tablet computer, a mobile computing device, a wearable computing device, a network appliance, a web appliance, a distributed computing system, a processor-based system, and/or a consumer electronic device.

In other embodiments, some or all of the components of the quality analysis system 302 and/or the imaging system 304 can be implemented as part of a cloud-based computing system. For example, in some embodiments, the quality analysis system 302 may be embodied as a "virtual server" formed from multiple computing devices distributed across a network and operating in a public or private cloud. In still other embodiments, some or all of the components of the quality analysis system 302 and/or the imaging system 304 can be components of the system 100, for example, such as part of the fabrication computing system 102 or the fabrication system 104. In yet other embodiments, some or all of the components of the quality analysis system 302 and/or the imaging system 304 may be distributed across various components of the system 100, for example, such as part of the thermoforming system 105 and part of the cutting system 106. Accordingly, although the quality analysis system 302 is illustrated in FIG. 3 as embodied in a single server computing device coupled to the imaging system 304, it should be appreciated that any of the quality analysis system 302 and the imagining system 304 may be embodied in multiple devices cooperating together to facilitate the functionalities described herein.

In some embodiments, the imaging system 304 generates or acquires a digital dental aligner (e.g., 2D images, 3D virtual model, and/or the like) for a corresponding fabricated dental aligner 130. For example, in some embodiments, the imaging system 304 may receive the fabricated dental aligner 130 from the fabrication system 104 to generate a corresponding digital dental aligner 310 from the fabricated dental aligner 130. In various embodiments, the imaging system 304 includes any suitable device, component, or combinations of devices or components configured to capture or generate the digital dental aligners 310 corresponding to digital representations of the fabricated dental aligners 130. For example, in some embodiments, the imaging system 304 includes a contour enhancing device 306 and an imaging device 308 to generate the digital dental aligners 310 from the fabricated dental aligners 130. While the contour enhancing device 306 and the imaging device 308 are shown as separate devices in FIG. 3, the present disclosure is not limited thereto, and in other embodiments, the contour enhancing device 306 and the imaging device 308 may be the same device, may be different devices, or may be parts of the same device or different devices.

In some embodiments, the contour enhancing device 306 may enhance the contours and features of the fabricated dental aligner 130, such that the contours and features can be detected by the imaging device 308 to generate the corresponding digital dental aligner 310. For example, in some embodiments, the fabricated dental aligner 130 may be a clear dental aligner, such that the contours and features of the fabricated dental aligner 130 may not be easily detected by the imaging device 308. In some embodiments, the contour enhancing device 306 may enhance the contours and features of the clear dental aligner 130, such that the imaging device 308 can detect the contours and features of the dental aligner 130 to generate the corresponding digital dental aligner 310. In various embodiments, the contour enhancing device 306 may include any suitable device, component, or combinations of devices or components configured to enhance the contours and features of the clear dental aligner 130, such that the contours and features can be detected by the imaging device 308 to generate the corresponding digital dental aligner 310 for inspecting the quality of the fabricated dental aligner 130.

For example, in some embodiments, the contour enhancing device 306 may emit light (e.g., a light beam, narrow light beam, or laser) into the dental aligner 130 such that the contours and features of the dental aligner 130 are enhanced. For example, in some embodiments, the light may be emitted into or onto the dental aligner 130 with a narrow beam angle, such that the beam angle allows the light to reflect off of at least a portion of the surface of dental aligner 130. In some embodiments, the narrow light beam can have a beam angle in the range of 1 to 30 degrees, 1 to 20 degrees, 4 to 15 degrees, 6 to 12 degrees, or 8 to 10 degrees. In some embodiments, the narrow light beam can have a beam angle that is less than 4 degrees, less than 6 degrees, less than 8 degrees, or less than 10 degrees. For example, a very narrow spot can be used to produce the narrow light beam and can have a beam angle of 7 degrees or less for a multifaceted reflector lamp or less than 15 degrees for a parabolic aluminized reflector lamp. In another example, a narrow spot can have a beam angle of 8 to 15 degrees for a multifaceted reflector lamp or 16 to 30 degrees for a parabolic aluminized reflector lamp. As used herein, beam angle may be determined by the angle between a point where the beam intensity is strongest (i.e., at a center directly beneath the light) to a point where the intensity of the light is 50% of the strongest intensity. In some embodiments, the light may be emitted into the dental aligner 130 at an oblique angle, such that the oblique lighting reflects off of surface imperfections in the dental aligner 130 differently than other parts of the dental aligner 130, or otherwise enables identification of the surface imperfections in the clear dental aligner material (e.g., through shadows or the like). In some embodiments, the light may be emitted at a particular spectrum of light corresponding to the material of the dental aligner 130, such that the light only transmits through surface imperfections of the dental aligner 130 or transmits in a different color through surface imperfections in the dental aligner 130 than through other parts of the dental aligner 130. In some embodiments, the light may only transmit through surface imperfections such as cracks, holes, bubbles, discolored areas, and/or the like in the dental aligner 130, or may transmit through surface imperfections in a luminance or color different from other parts of the dental aligner 130, such that any surface imperfections in the dental aligner 130 can be easily detected based on the color, spectrum, and/or luminance of the light emitted through the surface imperfections of the fabricated dental aligner 130. Accordingly, in some embodiments, the contour enhancing device 306 may enhance the surface imperfections of the fabricated dental aligner 130, such that the surface imperfections may be captured by the imaging device 308 to generate the corresponding digital dental aligners 310 (e.g., 2D views, virtual 3D model, or the like).

In another example, in some embodiments, the contour enhancing device 306 may transmit RF waves, acoustic waves (e.g., ultrasonic waves), or other wave mediums onto the dental aligner 130 such that the contours and features of the dental aligner 130 are enhanced. For example, in some embodiments, the RF waves or acoustic waves transmitted onto the dental aligner 130 may reflect off the material of the dental aligner 130 such that the imaging device 308 can generate the digital dental aligners 310 based on the reflection of the waves off the fabricated dental aligner 130. In another example, in some embodiments, the contour enhancing device 306 may transmit X-ray waves onto the dental aligner 130 to map the contours and features of the dental aligner 130, similar to a computer tomography scanning device (e.g., CAT scanning device).

In yet another example, in some embodiments, the contour enhancing device 306 may apply a suitable material or coating on the dental aligners 130 such that the contours and features of the dental aligner 130 are enhanced. For example, in some embodiments, the dental aligner 130 may be sprayed, dipped, coated, brushed, or otherwise prepared with a powder material (e.g., a starch material or a matted powder material) or a viscous material (e.g., food grade spray material) such that the shapes and geometries of the patient's dentition (e.g., shapes of teeth, gingival line, interproximal regions, and/or the like) in the clear dental aligner 130 can be detected by the imaging device 308. In some embodiments, the material or coating may be easily removable (e.g., washable, dissolvable, and/or the like) from the dental aligner 130, and/or may be safe for human consumption. In still another example, in some embodiments, the contour enhancing device 306 may apply thermal radiance to the dental aligner 130 that warms the contours and features of the dental aligner 130 differently from other parts of the dental aligner 130, and the imaging device 308 may include a thermal imaging device to detect the contours and features of the dental aligner 130. In yet other examples, the contour enhancing device 306 may include a grid array, needle array, light bed, or any other suitable device that enhances or otherwise enables detection of the contours and features of a clear dental aligner. While various examples of the contour enhancing device 306 are provided, the present disclosure is not limited thereto, and in other embodiments, the contour enhancing device 306 may be omitted, may use a combination of methods described herein to enhance the contours and features of a clear dental aligner, or may use other methods or combinations of methods to enhance the contours and features of a clear dental aligner, such that the contours and features may be captured by the imaging device 308 to generate a corresponding digital dental aligner 310.

In various embodiments, the imaging device 308 may include any suitable device, component, or combinations of devices or components configured to detect and capture various contours and features (e.g., shapes, geometries, surface imperfections, and/or the like) of the fabricated dental aligner 130 to generate one or more suitable digital dental aligners 310. A suitable digital dental aligner 310 is a digital representation (e.g., 2D image, virtual 3D model, or the like) of the fabricated dental aligner 130 that shows or describes the surface geometry (e.g., corresponding to the shapes and geometries of the patient's dentition) and/or surface imperfections (e.g., holes, cracks, bubbles, discoloration, and/or the like) of the fabricated dental aligner 130. For example, in some embodiments, a suitable digital dental aligner 310 may include various 2D image views of the fabricated dental aligner 130. In another example, in some embodiments, a suitable digital dental aligner 310 may include a virtual 3D model of the fabricated dental aligner 130. For example, in some embodiments, the suitable digital dental aligner 310 may be embodied as a three-dimensional (3D) representation (e.g., an STL file or the like) that describes the contours and features (e.g., surface geometry and/or surface imperfections) of the fabricated dental aligner 130. Accordingly, in some embodiments, the imaging device 308 may include a camera or other suitable imaging device to capture various views (e.g., 2D images) of the fabricated dental aligner 130. In some embodiments, the imaging system 305 may include any suitable scanning device or stereoscopic imaging device to capture digital scans (e.g., 3D scans) of the fabricated dental aligner 130. In other embodiments, the imaging device 308 may include any combinations of one or more cameras and one or more scanning devices to generate a plurality of digital dental aligners 310 corresponding to a fabricated dental aligner 130. For example, in some embodiments, the plurality of digital dental aligners 310 may include both 2D views of the fabricated dental aligner 130 and a virtual 3D model of the fabricated dental aligner 130.

For example, in some embodiments, the imaging device 308 may include a plurality of fixed cameras arranged around a fixed platform configured to hold the fabricated dental aligner 130 (e.g., while arranged on or removed from the dental mold) at a particular orientation, such that each of the fixed cameras captures a corresponding view of the fabricated dental aligner 130. In another example, the imaging device 308 may include one or more fixed cameras, and the platform may rotate or otherwise change the orientation of the fabricated dental aligner 130 such that the one or more fixed cameras can capture various views of the fabricated dental aligner 130. In still another example, the imaging device 308 may include one or more moveable cameras that rotate around a fixed platform to capture various views of the fabricated dental aligner 130. In yet another example, the imaging device 308 may include a moveable platform and at least one moveable camera that may each rotate or otherwise move with respect to the other to capture various views of the fabricated dental aligner 130. In some embodiments, the views of the fabricated dental aligner 130 may be captured by the imaging system 304 after (or while) the contours and features of the fabricated dental aligner 130 has been enhanced by the contour enhancing device 306. For example, in some embodiments, the various views of the fabricated dental aligner 130 may be captured by the imaging device 308 while the contour enhancing device 306 is emitting light (or other suitable wave medium) onto the fabricated dental aligner 130, such that the contours and features (e.g., surface imperfections) of the fabricated dental aligner 130 are enhanced or otherwise shown in the captured views. In some embodiments, the views of the fabricated dental aligner 130 may include various views of the fabricated dental aligner 130 while the fabricated dental aligner 130 is still arranged on the dental mold.

In some embodiments, the views may include, for example, a top down view with a cavity of the fabricated dental aligner 130 facing up, such that the imaging device 308 can capture a view of the cavity of the fabricated dental aligner 130. The top down view may capture, for example, the oblique lighting reflecting off of surface imperfections (e.g., cracks, holes, bubbles, areas of opacity, and/or the like) in the fabricated dental aligner 130. In some embodiments, the top down view may further provide a view of the corresponding dental arch associated with the fabricated dental aligner 130, a view of the teeth coverage of the dental aligner 130, a view of the edges (e.g., the cut edges) of the dental aligner 130, and/or the like. In some embodiments, the views may include, for example, the labial regions of the fabricated dental aligner 130. The labial region views may provide insights to various fit issues where the fabricated dental aligner 130 touches the patient's gums to cause irritation to the gums. The labial region views may also provide external front and side views of the cut edges of the dental aligner 130. Similarly, in some embodiments, the views may include, for example, the lingual regions of the fabricated dental aligner 130. The lingual region views may provide insights to various fit issues where the fabricated dental aligner 130 can cause irritation to the patient's tongue. The lingual region views may also provide internal front and side views of the cut edges of the dental aligner 130. In some embodiments, the views may include front and side views of the fabricated dental aligner 130 while still arranged on the dental mold. Such views may be provide insights into a general fit of the dental aligner 130 on the dental mold, such as a distance between the cavity surface of the dental aligner and the exterior surfaces of the dental mold (e.g., representing the teeth regions, gingiva regions, and/or the like).

In another example, in some embodiments, the imaging device 308 may include a scanning bed or other suitable scanning or stereoscopic imaging device. In this case, the imaging device 308 may generate a virtual 3D model of the fabricated dental aligner 130 embodied as a three-dimensional (3D) representation (e.g., an STL file or the like) that describes the surface geometries of the fabricated dental aligner 130. For example, in some embodiments, the fabricated dental aligner 130 may be scanned by the imaging device 308 after (or while) the contours and features of the fabricated dental aligner 130 has been enhanced by the contour enhancing device 306. For example, in some embodiments, the fabricated dental aligner 130 may be scanned by the imaging device 308 after enhancing material (e.g., matted powder, starch powder, starch spray, food grade spray, and/or the like) has been applied on the fabricated dental aligner 130 by the contour enhancing device 306, such that the contours and features of the clear material of the fabricated dental aligner 130 are detected by the imaging device 308 to generate the virtual 3D model of the fabricated dental aligner 130. However, the present disclosure is not limited thereto, and in other embodiments, the imaging device 308 may generate the virtual 3D model directly from the fabricated dental aligner 130, such that no enhancement of the contours and features of the fabricated dental aligner 130 is required by the contour enhancing device 306.

In some embodiments, the imaging device 308 may be configured to generate or acquire various 2D views of the dental mold used to form the dental aligner 130. For example, in some embodiments, if the digital dental aligners 310 include one or more 2D views of the fabricated dental aligner, the imaging device 308 may generate or acquire one or more corresponding 2D views of the dental mold used to fabricate the dental aligner 130 for comparison. In other embodiments, the imaging device 308 may generate or acquire corresponding 2D views of the patient's dentition from the dentition scans 108 or other model of the patient's dentition. In some embodiments, the 2D views of the dental mold may be acquired while the fabricated dental aligner 130 is still positioned on the dental mold. In other embodiments, the 2D views of the dental mold may be acquired after the fabricated dental aligner 130 is removed from the dental mold. In some embodiments, the 2D views of the dental mold may include views with the fabricated dental aligner 130 still positioned on the dental mold and views with the fabricated dental aligner 130 removed from the dental mold. In various embodiments, the imaging device 308 may provide the corresponding digital dentition (e.g., corresponding 2D views of the dental mold or other model of the patient's dentition) along with the corresponding 2D views of the fabricated dental aligner 130 in the digital dental aligners 310 to the image analyzer 318, or may store the corresponding digital dentition (e.g., in a storage device) for later retrieval.

In some embodiments, the imaging system 304 provides the digital dental aligners 310 to the quality analysis system 302 for further analysis. For example, in some embodiments, the quality analysis system 302 may analyze various 2D views and/or a virtual 3D model of the fabricated dental aligner 130, to determine whether there are any surface imperfections in the fabricated dental aligner 130. In some embodiments, the digital dental aligner 305 may be compared with a corresponding digital cut line file used to generate the cut line for the fabricated dental aligner 130 to ensure that the fabricated dental aligner 130 was cut properly from the dental mold. In some embodiments, the quality analysis system 302 may compare the digital dental aligner 310 with a digital representation of the patient's dentition (e.g., the 2D views or a 3D model of the patient's dentition) to ensure that the fabricated dental aligner 130 fits and/or conforms properly to the patient's dentition. For example, in some embodiments, the quality analysis system 302 may compare 2D views of the fabricated dental aligner 130 with corresponding 2D views of the dental mold used to form the fabricated dental aligner 130, with corresponding 2D views of another model (e.g., the dentition scans 108) of the patient's dentition, and/or with corresponding 2D direct views of the patient's dentition. In another example, in some embodiments, the quality analysis system 302 may compare a virtual 3D model of the fabricated dental aligner 130 with a 3D model of the patient's dentition (e.g., the dentition scans 108 or a scan of the dental mold). In various embodiments, the quality analysis system 302 may determine whether the dental aligner 130 was fabricated properly and/or cut correctly to fit comfortably in the patient's mouth through computer vision and computer comparison between the fabricated dental aligner 130 and the patient's dentition.

In some embodiments, the quality analysis system 302 may be embodied as or includes a processing circuit 312 including a processor 314 (or one or more processors) and memory 316. In some embodiments, the processor 314 may be embodied as any suitable type of processor capable of performing the functions described herein. The processor 314 may be embodied as a single-core or multi-core processor(s), digital signal processor, microcontroller, or other processor or processing/controlling circuit. The processor 314 can be a general purpose or specific purpose processor, an application specific integrated circuit (ASIC), one or more field programmable gate arrays (FPGAs), a group of processing components, or other suitable processing components. The processor 314 is configured to execute computer code or instructions stored in memory or received from other computer readable media (e.g., CDROM, network storage, a remote server, etc.).

Memory 316 may be embodied as any suitable type of volatile or non-volatile memory or data storage capable of performing the functions described herein. In operation, the memory 316 may store various data and software used during operation of the quality control system 300, such as operating systems, applications, programs, libraries, and drivers. In various embodiments, memory 316 can include one or more devices (e.g., memory units, memory devices, storage devices, etc.) for storing data and/or computer code for completing and/or facilitating the various processes described in the present disclosure. Memory 316 can include random access memory (RAM), read-only memory (ROM), hard drive storage, temporary storage, non-volatile memory, flash memory, optical memory, or any other suitable memory for storing software objects and/or computer instructions. Memory 316 can include database components, object code components, script components, or any other type of information structure for supporting the various activities and information structures described in the present disclosure. Memory 316 may be communicably connected to the processor 314 via the processing circuit 312, and may include computer code for executing (e.g., by processor 314) one or more processes described herein.

Still referring to FIG. 3, in an illustrative embodiment, memory 316 includes a surface analyzer 318, a feature mapper 320, a comparator 322, and a dental mold analyzer 324. In other embodiments, memory 315 may include more or less components than those shown in FIG. 3 depending on the types of digital dentitions 310 (e.g., 2D views or 3D models) and/or features of the fabricated dental aligner 130 being analyzed by the quality analysis system 302. In some embodiments, the surface analyzer 318 receives the digital dental aligners 310 from the imaging system 304, and analyzes the digital dental aligners 310 (e.g., 2D views or virtual 3D model) to determine whether there are any surface imperfections or other abnormal or anomalous quality characteristics in the digital dental aligners 310. For example, in some embodiments, any surface imperfections in the digital dental aligners 310 may be enhanced by the contour enhancing device 306, such that the digital dental aligners 310 represent the surface imperfections differently than other parts of the corresponding fabricated dental aligner 130.

For example, in some embodiments, the surface analyzer 318 may be configured to identify a surface imperfection in the fabricated dental aligner 130 from the digital dental aligner 310 based on an expected spectrum or luminance of light transmitted through (or by) the fabricated dental aligner 130, such that any portion of the fabricated dental aligner 130 that transmits light outside an expected range (e.g., a threshold range) of the expected spectrum or luminance may be determined to be a portion (or area) of the fabricated dental aligner 130 having a surface imperfection (e.g., hole, crack, bubble, discoloration, areas of opacity, or the like). For example, in some embodiments, if the fabricated dental aligner 130 transmits disparate portions of light outside the expected range, this may indicate a crack, hole, or bubble in those disparate portions. In another example, in some embodiments, if a majority (or a large continuous portion) of the fabricated dental aligner 130 transmits light that is outside the range, this may indicate clarity issues or discoloration of the fabricated dental aligner 130. However, the present disclosure is not limited thereto, and in other embodiments, the surface imperfections may be detected in the fabricated dental aligner 130 from other wave mediums (e.g., RF waves, acoustic waves, X-ray waves, and/or the like) reflecting or transmitting differently off the surface imperfections, or from a mapping of the contours and features of the fabricated dental aligner 130 captured directly by the imaging device 308 (e.g., without the contours and features being enhanced by the contour enhancing device 306).

In some embodiments, the surface analyzer 318 may learn (e.g., using machine learning or data mining) to identify the surface imperfections in the digital dental aligners 310. For example, in some embodiments, the surface analyzer 318 may be provided with training data including examples of dental aligners with surface imperfections and examples of dental aligners without (or with minimal) surface imperfections, such that the surface analyzer 318 can learn from the training data to identify the surface imperfections in the digital dental aligners 310. In some embodiments, the training data may include examples with the surface imperfections enhanced (e.g., via the contour enhancing device 306) and/or with the surface imperfections not enhanced, such that the surface analyzer 318 may learn to detect the surface imperfections with and/or without the surface imperfections being enhanced. In some embodiments, the surface analyzer 318 may utilize various suitable machine learning methodologies (e.g., classification, regression, clustering, and/or the like) to distinguish between surface imperfections and other contours and features of a fabricated dental aligner.

In some embodiments, the feature mapper 320 identifies and maps various shapes and geometries of the fabricated dental aligner 130 shown in the corresponding digital dental aligner 310. For example, in some embodiments, the feature mapper 320 may include a suitable object detection or edge detection algorithm to identify and map the shapes and geometries of the fabricated dental aligner 130 shown in one or more 2D views of the corresponding digital dental aligner 310. In some embodiments, the shapes and geometries may include, for example, edges (e.g., cut edges) where the fabricated dental aligner 130 was cut from the dental mold as shown in the one or more 2D views, various outlines or shapes (e.g., creases, gaps, identifiable tooth portion shapes, identifiable gingival line portion shapes, and/or the like) shown in the one or more 2D views, dimensions (e.g., height, width, length) of the fabricated dental aligner 130 shown in the one or more 2D views, thickness of the thermoformed material at the edges shown in the one or more 2D views, and/or the like. In some embodiments, if the 2D views include views of the dental aligner 130 while still arranged on the dental mold, the feature mapper 320 may measure and map distances between the inner surface of the dental aligner and an outer surface of the dental mold as shown through the clear dental aligner material. In some embodiments, the feature mapper 320 may similarly map various shapes and geometries of the patient's dentition shown in the corresponding 2D views of the digital dentitions.

In another example, in some embodiments, the feature mapper 320 may identify and map various shapes and geometries of the fabricated dental aligner 130 shown in a virtual 3D model of the fabricated dental aligner. For example, in some embodiments, the feature mapper 320 may identify and map teeth portions in the virtual 3D model of the fabricated dental aligner 130, and may identify and map a gingival line or gingival line portions in the virtual 3D model of the fabricated dental aligner 130. In some embodiments, the feature mapper 320 may identify the teeth portions in the virtual 3D model of the fabricated dental aligner 130 using a suitable identification algorithm. For example, in some embodiments, the feature mapper 320 may identify various characteristics within the virtual 3D model of the fabricated dental aligner 130 that are consistent with teeth, such as surface contours of crowns, separation or gaps in the interproximal region (e.g., the space between teeth), and/or the like, such that the teeth portions within the virtual 3D model of the fabricated dental aligner 130 can be identified, and the remaining portions which are not identified as the teeth portions may be identified as gingiva portions.

In some embodiments, the feature mapper 320 may identify and map the gingival line or gingival line portions from the virtual 3D model of the fabricated dental aligner 130. For example, in some embodiments, the feature mapper 320 may be configured to identify the gingival line or gingival line portions by identifying a location where the teeth portions and gingiva portions meet. As described above, the feature mapper 320 may be configured to identify a location of the teeth portions within the virtual 3D model of the fabricated dental aligner 130, and may identify the location of the gingiva portions based on the portions that are not identified as the teeth portions. Similarly, the feature mapper 320 may identify and map the gingival line or gingival line portions in each of the digital representations based on where the portions identified as the teeth portions meet the portions identified as the gingiva portions. In some embodiments, the feature mapper 320 may map edges of the virtual 3D model where the dental aligner was cut from the dental mold. In some embodiments, the feature mapper 320 may generate a point cloud for the virtual 3D model of the fabricated dental aligner 130. The point cloud may describe the surface features and/or edges of the virtual 3D model as a set of surface points. In some embodiments, the point cloud may describe all of the surface points identified by the feature mapper 320, or may describe key points (e.g., key teeth, key locations on the gingival line, back portions of the molar regions, key locations along the edges, and/or the like). In some embodiments, the feature mapper 320 may similarly map the teeth portions, gingival line portions, and/or point cloud in the corresponding 3D model of the patient's dentition.

In some embodiments, the feature mapper 320 may map a digital cut line for the digital dental aligners 310. For example, in some embodiments, the feature mapper 320 may identify a digital cut line file corresponding to the fabricated dental aligner 130. In some embodiments, the feature mapper 320 may map the cut line (or a portion of the cut line) corresponding to the digital cut line file of the digital dental aligner 310. For example, in some embodiments, the feature mapper 320 may add and map a portion of the cut line in each of the 2D views of the fabricated dental aligner 130. In another example, in some embodiments, the feature mapper 320 may add and map the cut line in the virtual 3D model of the fabricated dental aligner 130. In some embodiments, the feature mapper 320 may similarly add and map the cut line or portions of the cut line in the digital dentition. However, the present disclosure is not limited thereto, and in other embodiments, the feature mapper 320 may not add or map the digital cut line on the digital dental aligner 310 or the digital dentition, and the digital cut line file used to cut the fabricated dental aligner 130 from the dental mold may be compared directly with the mapped edges in the digital dental aligner 310.

In some embodiments, the comparator 322 may analyze the mappings or other quality characteristics of the digital dental aligner 310 to determine whether the corresponding fabricated dental aligner was formed properly to fit the patient's corresponding dental arch. In some embodiments, the comparator 322 may compare the digital dental aligner 310 with the digital dentition (e.g., 2D views or 3D model representation of the patient's dentition). For example, in some embodiments, the comparator 322 may compare various quality characteristics of the fabricated dental aligner 130 with those of the patient's dentition, such as the shapes and geometries mapped in each of the 2D views of the fabricated dental aligner 130 with the shapes and geometries mapped in the corresponding 2D views of the dental mold or other model of the patient's dentition to determine whether the shapes and geometries of the fabricated dental aligner 130 matches the shapes and geometries of the patient's dentition. For example, in some embodiments, the comparator 322 may overlay a top down view of the fabricated dental aligner 130 with a corresponding view of the dental mold, such that a shape of the arch of the fabricated dental aligner 130 can be compared with a shape of the corresponding arch of the patient's dentition. The top down view comparison may also indicate whether the fabricated dental aligner 130 properly covers all the teeth of the corresponding arch of the patient's dentition. In another example, in some embodiments, the comparator 322 may similarly overlay a side view of the fabricated dental aligner 130 with a corresponding view of the dental mold, such that the shapes and geometries shown in the side views can be compared. In some embodiments, the comparator may overlay the corresponding views using a best fit algorithm such that the mapped shapes, outlines, edges, cut line, and/or the like are aligned or substantially aligned. In some embodiments, the comparator may compare the mapped distance between the inner surface of the dental aligner and the exterior surface of the dental mold with a threshold value or range to determine whether the mapped distance is within tolerance. In some embodiments, if the mapped distance is within tolerance, the fabricated dental aligner 130 may be determined to properly fit the patient's dentition.

In another example, in some embodiments, the comparator 322 may overlay a virtual 3D model of the dental aligner 130 on a corresponding 3D model of the patient's dentition, such that the shapes and geometries of the fabricated dental aligner 130 can be compared with the shapes and geometries of the patient's dentition. For example, in some embodiments, the comparator 322 may identify one or more common points (or other common locations) in each of the virtual 3D model of the dental aligner 130 and the 3D model of the patient's dentition, and may align the geometries of each of the models based on the one or more common points. In some embodiments, after aligning the one or more common points, the virtual 3D model of the dental aligner 130 may still be separated from the 3D model of the patient's dentition by a distance due to difficulties with perfectly overlaying two virtual surfaces with zero separation between them. In some embodiments, the comparator 322 may determine whether the distance between the overlaid virtual 3D model of the dental aligner 130 and the 3D model the patient's dentition is within tolerance. For example, in some embodiments, the comparator 322 may calculate a root mean square (RMS) value (or values) between the point clouds of the virtual 3D model of the fabricated dental aligner 130 and the 3D model of the patient's dentition. In some embodiments, the RMS value may be calculated from each point in the point clouds, or from key points (e.g., key teeth, key locations, and/or the like) in the point clouds. In some embodiments, the comparator 322 may compare the calculated RMS value with a threshold value (or range) to determine whether the RMS value is within tolerance. In some embodiments, an RMS value that is within tolerance may indicate that the shapes and geometries of the 3D models correspond to each other (e.g., are the same).

In some embodiments, the comparator 322 may compare a thickness of the dental aligner 130 with a corresponding thickness threshold value or range. In some embodiments, the thickness of the dental aligner 130 may determine whether the fabricated dental aligner 130 is suitable to apply a force on the teeth to move the teeth to a desired position (e.g., based on the treatment plan). For example, if the dental aligner 130 is too thin (or has thin portions), the dental aligner 130 may not be able to generate enough force on the teeth to move the teeth to the desired position or the dental aligner may be more likely to break or wear out earlier than intended. Accordingly, in some embodiments, the comparator 322 may determine whether the thickness of the dental aligner 130 is within tolerance for a given thermoformed material and/or stage of the treatment plan.

In some embodiments, the comparator 322 may compare the digital dental aligner 310 with the digital cutline file. For example, in some embodiments, if the feature mapper 320 maps the digital cut line in the 2D views and/or the virtual 3D model of the fabricated dental aligner 130, then the comparator 322 may compare the mapped edges of the fabricated dental aligner 310 shown in the digital dental aligner 310 with the mapped digital cut line. For example, in some embodiments, the comparator 322 may calculate a distance between one or more points along the mapped edge and one or more corresponding points along the mapped cut line to determine if the distance is within tolerance (e.g., within a threshold value or range). If the distance is within tolerance, this may indicate that the fabricated dental aligner 130 was cut properly. In some embodiments, a preferred tolerance range may be, for example, one-quarter millimeter to one-half millimeter, but the present invention is not limited thereto.

In another example, in some embodiments, the comparator 322 may compare the digital dental aligner 310 directly with the digital cut line file used to form the fabricated dental aligner 130. For example, in some embodiments, the comparator 322 may compare the mapped edges in each 2D view of the fabricated dental aligner 130 with the corresponding cut line file to determine whether the mapped edges correspond to the cut line in the digital cut line file. For example, in some embodiments, the comparator 322 may calculate a distance between one or more points along the mapped edge and one or more corresponding points along the cut line to determine if the distance is within tolerance (e.g., within a threshold value or range). If the distance is within tolerance, this may indicate that the fabricated dental aligner 130 was cut properly. In another example, in some embodiments, the comparator 322 may compare the mapped edges in the virtual 3D model of the fabricated dental aligner 130 with the digital cut line file. For example, in some embodiments, the comparator 322 may overlay the virtual 3D model of the fabricated dental aligner 130 with the cut line in the digital cut line file by aligning a common point (or common location) in each of the virtual 3D model and the cut line, and calculating a distance between the mapped edge and the cut line. For example, in some embodiments, the comparator 322 may calculate an RMS value between points along the mapped edges in the virtual 3D model and corresponding points along the digital cut line to determine whether the RMS value is within threshold (e.g., a threshold value or range). If the RMS value is within tolerance, this may indicate that the fabricated dental aligner 130 was cut properly.

In various embodiments, if the surface analyzer 318 and/or the comparator 322 determines that the fabricated dental aligner 130 includes any anomalous portions (e.g., surface imperfections, areas that do not correspond to the shapes and geometries of the patient's dentition, and/or areas of the mapped edges that do not correspond to the digital cut line file), then the fabricated dental aligner 130 may be flagged indicating that the fabricated dental aligner 130 is rejected or is a potential reject. In some embodiments, the quality analysis system 302 may provide a graphical user interface to a dental technician (or other professional) to review any potential rejects to determine whether the identified anomalous portion warrants rejection of the corresponding fabricated dental aligner 130. In some embodiments, the quality analysis system 302 may highlight the identified anomalous portions in a view of the digital dental aligner in the graphical user interface, such that the anomalous portions can be quickly identified from the view. In some embodiments, any flagged dental aligner 130 may cause the fabrication computing system 102 to fabricate a replacement dental aligner 130 for the corresponding patient.

In some embodiments, the dental mold analyzer 324 may analyze various views of the dental mold used to fabricate the dental aligner 130. For example, in some embodiments, the dental mold analyzer 324 may analyze the various views to determine whether the dental mold has any issues (e.g., breaches, cracks or holes in the wall, burns or abrasions, and/or the like). For example, in some embodiments, the dental mold may include a powder packet (e.g., a nylon powder) that may indicate when the cut is too deep or otherwise at an incorrect location. For example, in some embodiments the powder may be of a different contrasting color than the fabricated dental aligner 130, such that when a breach occurs, the powder may be detected in the various views of the dental mold. In some embodiments, the views of the dental mold may be analyzed to determine whether any anomalous portions identified in the fabricated dental aligner 130 was caused by the dental mold in response to the fabricated dental aligner 130 being flagged as a reject or potential reject. In some embodiments, the views of the dental mold may be analyzed to determine whether the dental mold can be used to form subsequent dental aligners for the patient in response to the fabricated dental aligner 130 passing inspection.

In some embodiments, the dental mold analyzer 324 may determine whether a breach occurred during cutting of the fabricated dental aligner 130 from the dental mold. For example, in some embodiments, the dental mold analyzer 324 may receive particulate detection data from the cutting system 106, and may analyze the particulate detection data to determine whether the powder material of the powder packet was detected. For example, in some embodiments, the powder material in the powder packet may be much smaller (e.g., 70 microns) than waste material generated from cutting the fabricated dental aligner. In this case, the breached powder material may be detected based on the size of the particulates in the particulate data.

Figure 4:
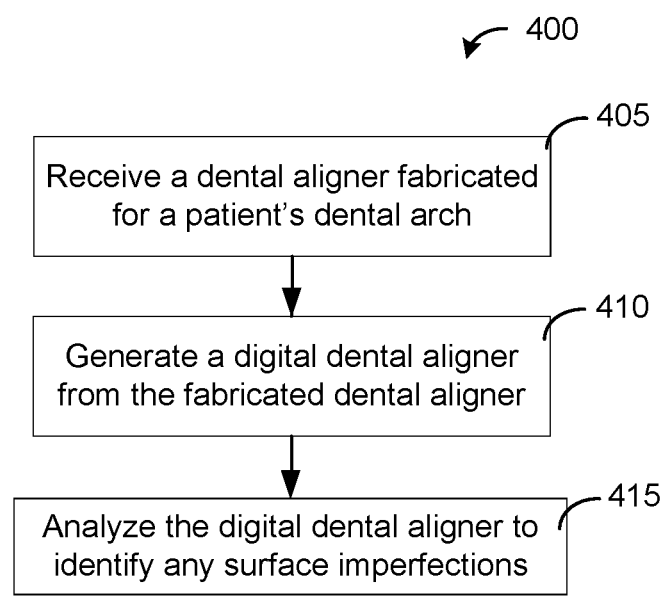
FIG. 4 is a flow diagram of a method for analyzing surface quality of fabricated dental aligners, according to an illustrative embodiment.

FIG. 4 is a flow diagram of a method for analyzing quality of fabricated dental aligners, according to some embodiments. The functionalities of the method 400 may be implemented using, or performed by, the components detailed herein in connection with FIGS. 1 and 3. In brief overview, the method 400 of FIG. 4 may be used, for example, to determine whether a fabricated intraoral device, such as the dental aligner 130 shown in FIG. 2, was manufactured properly without surface imperfections.

Referring to FIG. 4, at operation 405, a dental aligner fabricated for a patient's dental arch is received. In various embodiments, the dental aligner may be fabricated by the system 100 shown in FIG. 1, or by any suitable intraoral device fabrication systems or methods. In some embodiments, the fabricated dental aligner may be received after it has been removed from a dental mold. In some embodiments, the fabricated dental aligner may be received while it is still arranged on the dental mold.

At operation 410, a digital dental aligner is generated from the fabricated dental aligner. In some embodiments, the digital dental aligner may include one or more 2D views of the fabricated dental aligner. In some embodiments, the one or more 2D views may include views of the fabricated dental aligner while still arranged on the dental mold and/or views of the fabricated dental aligner removed from the dental mold. In some embodiments, the digital dental aligner may include a virtual 3D model of the fabricated dental aligner. For example, in some embodiments, the imaging system 304 may generate a virtual 3D model of the fabricated dental aligner by scanning the fabricated dental aligner using the imaging device 308 (e.g., a suitable scanning device or stereoscopic imaging device).

In some embodiments, the fabricated dental aligner may be a clear dental aligner, such that the contours and features of the fabricated dental aligner may not be easily detected by the imaging device 308. In some embodiments, the contours and features of the fabricated dental aligner may be enhanced (e.g., by the contour enhancing device 306), such that the imaging device 208 can generate a suitable digital dental aligner for further analysis. A suitable digital dental aligner is a digital representation (e.g., 2D image, 3D model, or the like) of the fabricated dental aligner that sufficiently shows and/or describes the contours and features of the fabricated dental aligner to enable identification of the contours and features. Accordingly, in some embodiments, the imaging system 304 may enhance the contours and features of the fabricated dental aligner such that the contours and features of the fabricated dental aligner can be captured by the imaging device 308. For example, in various embodiments, the contour enhancing device 306 may apply light, radio waves, acoustic waves, x-rays, thermal radiance, enhancing material, and/or the like to a surface of the fabricated dental aligner, such that various contours and features of the clear material of the fabricated dental aligner is enhanced to enable the imaging device 108 to capture the enhanced contours and features.

At operation 415, the digital dental aligner is analyzed to identify any surface imperfections in the fabricated dental aligner. For example, in some embodiments, the imaging system 304 may provide the digital dental aligner to the quality analysis system 302 for analysis. In some embodiments, the surface analyzer 318 may analyze the digital dental aligner to identify any surface imperfections in the fabricated dental aligner. For example, in some embodiments, the surface analyzer 318 may be configured to identify the surface imperfections from the enhanced contours and features shown in the digital dental aligner. For example, in some embodiments, the surface analyzer 318 may detect anomalous portions (e.g., surface imperfections) where light is transmitted differently at the anomalous portions than other portions of the fabricated dental aligner.

Figure 5:
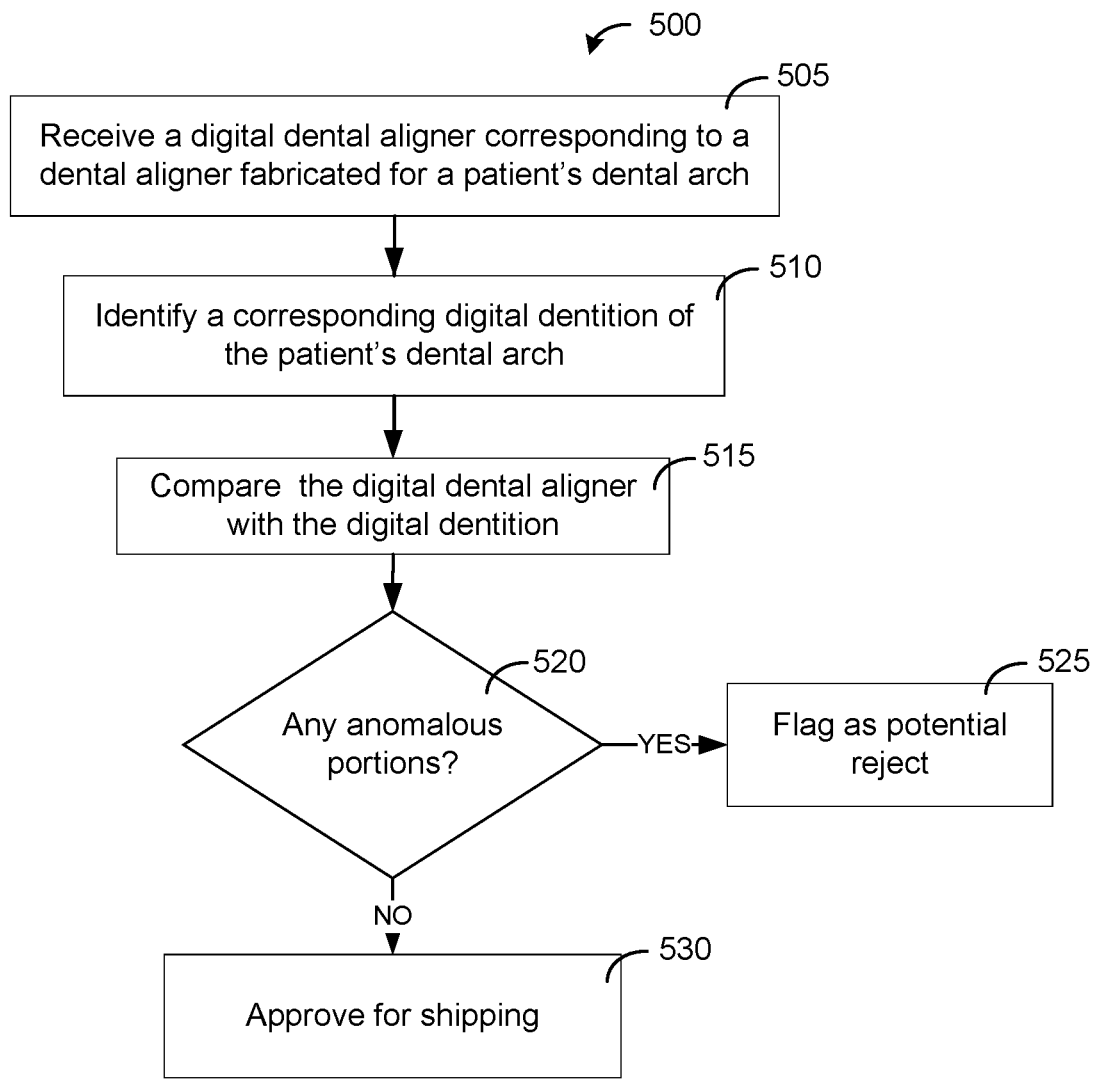
FIG. 5 is a flow diagram of a method for analyzing fit quality of fabricated dental aligners, according to an illustrative embodiment.

FIG. 5 is a flow diagram of a method for analyzing the quality of fabricated dental aligners, according to some embodiments. The functionalities of the method 500 may be implemented using, or performed by, the components detailed herein in connection with FIGS. 1 and 3. In brief overview, the method 500 of FIG. 5 may be used, for example, to determine whether a fabricated intraoral device, such as the dental aligner 130 shown in FIG. 2, was properly manufactured to move the patient's teeth as intended by the treatment plan.

Referring to FIG. 5, at operation 505, a digital dental aligner corresponding to a dental aligner fabricated for a patient's dental arch is received. In various embodiments, the dental aligner may be fabricated by the system 100 shown in FIG. 1, or by any suitable intraoral device fabrication systems or methods. In some embodiments, the digital dental aligner may include one or more views (e.g., 2D views) of the fabricated dental aligner. In some embodiments, the digital dental aligner may include a virtual 3D model of the fabricated dental aligner. For example, in some embodiments, the fabricated dental aligner may be photographed, scanned, and/or the like by the imaging system 304 such that the digital dental aligner is generated by and received from the imaging system 304. In some embodiments, the contours and features of the fabricated dental aligner may be enhanced (e.g., by the contour enhancing device 306), such that the contours and features (e.g., surface imperfections, shapes, geometries, edges, and or the like) of the fabricated dental aligner are enhanced or otherwise shown in the corresponding digital dental aligner.

At operation 510, a corresponding digital dentition of the patient's dental arch is identified. In some embodiments, the digital dentition may corresponding to a digital representation (e.g., one or more 2D views, a 3D model, or the like) of the patient's dental arch corresponding to the fabricated dental aligner. For example, in some embodiments, the digital dentition may include one or more views (e.g., 2D views) of the dental mold used to form the fabricated dental aligner. In other embodiments, the digital dentition may include one or more views (e.g., 2D views) of another model representing the patient's dental arch (e.g., views of the dental scans 108 or of a physical dental impression). In another example, in some embodiments, the digital dentition may include a 3D model (e.g., the dentition scans 108 or a scan of the dental mold) of the patient's dental arch. In various embodiments, the digital dentition may be generated and received from the imaging device 308, or may be retrieved from storage (e.g., a storage device).

At operation 515, the digital dental aligner is compared with the digital dentition. For example, in some embodiments, the contours and features of the fabricated dental aligner identified in the digital dental aligner are compared with the contours and features of the corresponding digital dentition of the patient's dental arch. In some embodiments, the digital dental aligner may be overlaid with the digital dentition to compare the contours and features of the digital dental aligner with the contours and features of the digital dentition. In some embodiments, the digital dental aligner may be compared with a digital cut line file used to cut the fabricated dental aligner from the dental mold.

Accordingly, at operation 520, any anomalous portions between the comparison of the digital dental aligner and the corresponding digital dentition are identified. For example, in some embodiments, an anomalous portion may correspond to a portion where a shape, geometry, or surface feature of the fabricated dental aligner does not correspond to (e.g., overlap with, line up with, or the like) a shape, geometry, or surface feature of the patient's corresponding dentition. In this case, the identified anomalous portion may indicate that the fabricated dental aligner may include surface imperfections, may not match the patient's dentition properly, may not have been cut properly, and/or the like, and thus, may not fit comfortably in the patient's mouth or be configured to move the patient's teeth as intended by the treatment plan. Accordingly, in some embodiments, in response to identifying any anomalous portions at operation 520 (e.g., YES), the corresponding fabricated dental aligner may be flagged as a reject or potential reject at operation 525. In some embodiments, any flagged dental aligners may be provided to a dental technician (or other professional) for further review. In some embodiments, any flagged dental aligner 130 may cause the fabrication computing system 102 to fabricate a replacement dental aligner 130 for the corresponding patient. On the other hand, in some embodiments, in response to determining that there are no anomalous portions from the comparison at operation 520 (e.g., NO), the corresponding fabricated dental aligner may be approved for shipping to the patient at operation 530.

Figure 6:
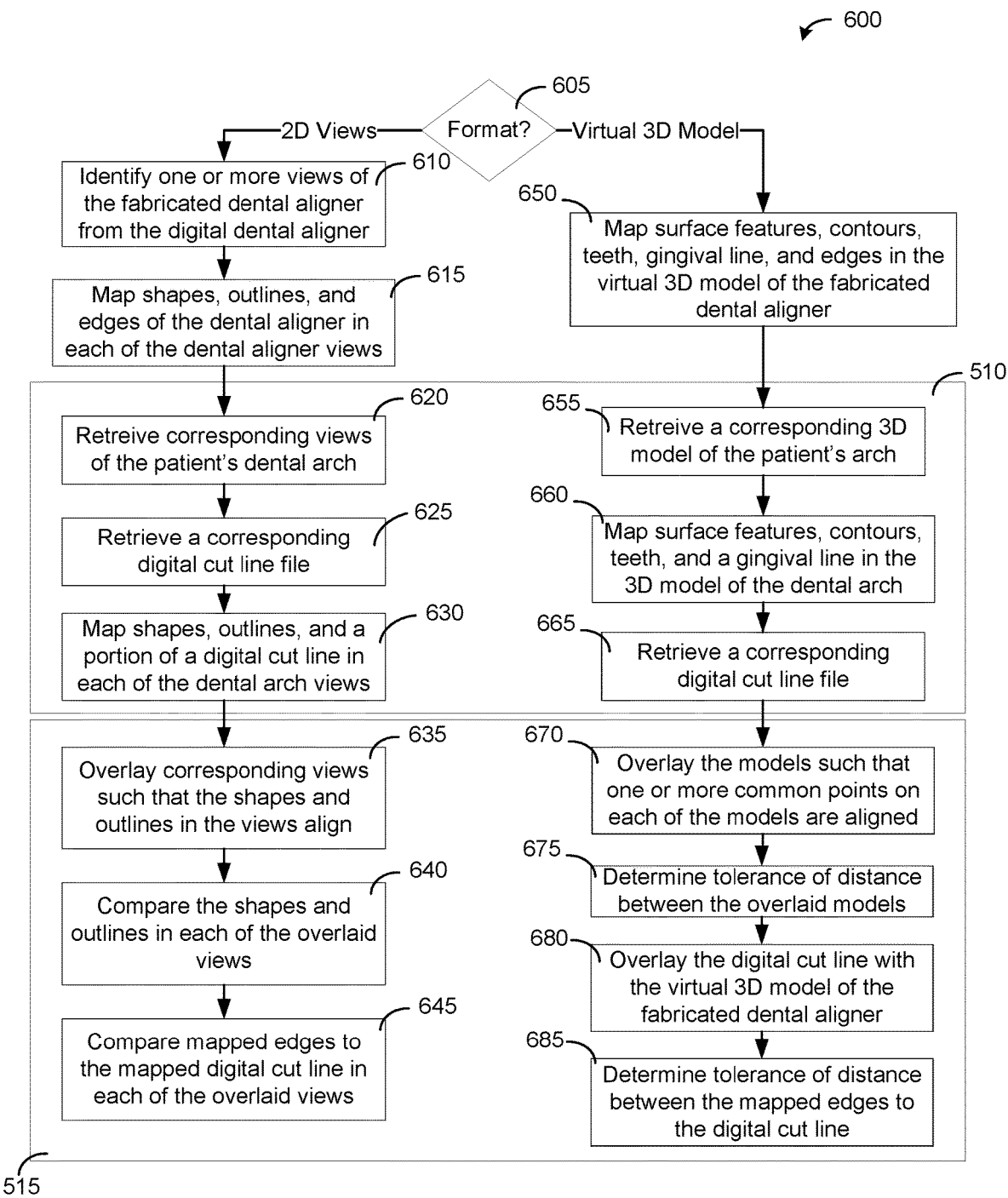
FIG. 6 is a flow diagram of a method for analyzing the quality of fabricated dental aligners, according to another illustrative embodiment.

FIG. 6 is flow diagram of a method for analyzing the quality of fabricated dental aligners, according to some embodiments. The functionalities of the method 600 may be implemented using, or performed by, the components detailed herein in connection with FIGS. 1 and 3. In brief overview, the method 600 of FIG. 6 may be used in connection with the method 500 of FIG. 5, for example, to determine whether a fabricated intraoral device, such as the dental aligner 130 shown in FIG. 2, was fabricated properly to be worn comfortably in the patient's mouth and to move the patient's teeth as intended by the treatment plan. For example, in some embodiments, the method 600 may include operations 620, 625, 630, 655, 660, and 665 corresponding to the operation 510 of FIG. 5, and operations 635, 640, 645, 670, 675, 680, and 685 corresponding to operation 515 of FIG. 5.

Referring to FIG. 6, in response to receiving a digital dental aligner, a format of the received digital dental aligner is determined at operation 605. In some embodiments, for example, at operation 605, the surface analyzer 318 (or the feature mapper 320) may determine whether the digital representations of the fabricated dental aligner include one or more 2D views (e.g., 2D images) of various views of the fabricated dental aligner, and/or a virtual 3D model of the fabricated dental aligner. In some embodiments, if the digital representations of the fabricated dental aligner includes one or more 2D views of the fabricated dental aligner at operation 605, then a view of each of the 2D images of the fabricated dental aligner is identified at operation 610, and any identifiable shapes, outlines, and edges of the dental aligner in each of the 2D views are mapped at operation 615.

In some embodiments, if the digital representations of the fabricated dental aligner include a virtual 3D model of the fabricated dental aligner at operation 605, then the surface features, contours, teeth, gingival line, and edges of the fabricated dental aligner shown in the virtual 3D model are mapped at operation 650. For example, in some embodiments, the feature mapper 318 may map the shapes, outlines, and edges shown in each of the 2D views of the fabricated dental aligner at operation 615, or the feature mapper 318 may map the surface features, contours, teeth, gingival line, and edges shown in the virtual 3D model of the fabricated dental aligner at operation 650.

In some embodiments, a corresponding digital dentition of the patient's dental arch is identified. For example, in some embodiments, if the digital dental aligner includes the 2D views of the fabricated dental aligner, corresponding views of the patient's dental arch are retrieved at operation 620. For example, in some embodiments, the imaging system 304 may capture various 2D views of the dental mold used to fabricate the dental aligner, and may provide the views of the dental mold to the quality analysis system 302 for further analysis. In some embodiments, each view of the dental mold may correspond to a view of the fabricated dental aligner, such that the views can be compared. In some embodiments, the identifiable shapes and outlines in each of the 2D views of the dental mold are mapped at operation 630, such that the shapes and outlines of the dental mold shown in the 2D views of the dental mold can be compared with the shapes and outlines of the fabricated dental aligner shown in the 2D views of the fabricated dental aligner. For example, in some embodiments, the feature mapper 320 may identify and map the shapes and geometries of the fabricated dental aligner 130 shown in one or more 2D views of the corresponding digital dental aligner 310. For example, the shapes and geometries may include, various outlines or shapes (e.g., creases, gaps, identifiable tooth portion shapes, identifiable gingival line portion shapes, and/or the like) in the one or more 2D views, dimensions (e.g., height, width, length) of the fabricated dental aligner 130 in the one or more 2D views, thickness of the thermoformed material at edges in the one or more 2D views, and/or the like.

In some embodiments, a corresponding digital cut line file is retrieved at operation 625. For example, in some embodiments, the corresponding digital cut line file may be the cut line file used to cut the fabricated dental aligner from the dental mold. In some embodiments, a corresponding portion of the cut line may be mapped in each of the 2D views of the dental mold at operation 625. For example, in some embodiments, the feature mapper 320 may map or add a corresponding portion of the cut line in each of the 2D views of the dental mold that shows a portion of the edges of the fabricated dental aligner, such that the edges shown in the 2D views of the fabricated dental aligner can be compared with a corresponding portion of the cut line shown in the 2D views of the dental mold. However, the present disclosure is not limited thereto, and in other embodiments, each of the 2D views of the dental aligner may be compared directly with the digital cut line file to determine whether the fabricated dental aligner was cut properly from the dental mold.

In another example, in the case that the digital dental aligner includes the virtual 3D model of the fabricated dental aligner, a corresponding 3D model of the patient's dental arch is retrieved at operation 655. For example, in some embodiments, the 3D model of the patient's dental arch may correspond to a digital scan of the patient's dental impression (e.g., the dentition scans 108), or the imaging system 304 may scan the dental mold used to fabricate the dental aligner to generate a 3D model of the dental mold. For example, in some embodiments, the 3D model of the patient's dental arch may be embodied as a three-dimensional (3D) representation (e.g., an STL file or the like) that describes the contours and features (e.g., surface features, contours, teeth portions, a gingival line, and/or the like) of the patient's dental arch. In some embodiments, the surface features, contours, teeth, and gingival line shown in the 3D model of the patient's dental arch are mapped at operation 660, such that the surface contours and features of the virtual 3D model of the fabricated dental aligner can be compared with the surface contours and features of the patient's dental arch as shown in the 3D model of the patient's dental arch. For example, the feature mapper 320 may identify and map teeth portions in the virtual 3D model of the fabricated dental aligner 130, and may identify and map a gingival line or gingival line portions in the virtual 3D model of the fabricated dental aligner 130.

In some embodiments, a corresponding digital cut line file is retrieved at operation 665. For example, in some embodiments, the corresponding digital cut line file may be the cut line file used to cut the fabricated dental aligner from the dental mold. In some embodiments, the corresponding digital cut line file may be retrieved at operation 665, such that the virtual 3D model of the fabricated dental aligner may be directly compared with a digital cut line in the corresponding digital cutline file. For example, in some embodiments, the feature mapper 320 or the comparator 322 may retrieve the digital cut line file from a storage device (e.g., a data store or data base) or may receive the digital cut line file from the model analyzer 118 to compare the virtual 3D model of the fabricated dental aligner with the digital cut line file. However, the present disclosure is not limited thereto, and in other embodiments, a digital cutline corresponding to the digital cut line file may be mapped or added to the 3D model of the patient's dental arch (e.g., via the feature mapper 320) for comparison with the edges mapped in the virtual 3D model of the fabricated dental aligner.

In some embodiments, if the digital dental aligner includes the 2D views of the fabricated dental aligner, such that corresponding views of the patient's dental arch are retrieved and mapped at operation 630 (e.g., via the feature mapper 320), each of the views of the fabricated dental aligner may be compared with corresponding views of the patient's dental arch. For example, in some embodiments, at operation 635, the comparator 322 may overlay corresponding views of the fabricated dental aligner and the patient's dental arch such that the shapes and outlines in the views align. In some embodiments, at operation 640, the shapes and outlines in each of the overlaid views are compared. In some embodiments, at operation 645, the mapped edges in the views of the fabricated dental aligner are compared with the mapped digital cut line in the views of the patient's dental arch. Accordingly, in some embodiments, the method 600 of FIG. 6 continues at operation 520 of FIG. 5, for example, to determine whether the comparisons result in the identification of any anomalous portions in the views of the fabricated dental aligner.

As another example, in the case that the digital dental aligner includes a virtual 3D model of the fabricated dental aligner, such that a corresponding 3D model of the patient's dental arch is retrieved and mapped at operation 660 (e.g., via the feature mapper 320), the virtual 3D model of the fabricated dental aligner may be compared with the 3D model of the patient's dental arch. For example, in some embodiments, at operation 670, the comparator 322 may overlay the models such that one or more common points on each of the models are aligned. In some embodiments, at operation 675, a tolerance between the models is determined. For example, in some embodiments, the comparator 322 may calculate an RMS value between the models, and may determine whether the RMS value is within a threshold range (or value). In some embodiments, at operation 680, the comparator 322 may overlay the virtual 3D model of the fabricated dental aligner with the digital cut line of the digital cut line file. For example, in some embodiments, the comparator 322 may overlay the virtual 3D model of the fabricated dental aligner with the digital cut line such that one or more common points on each of the cut lines and mapped edges are aligned. In some embodiments, at operation 685, a tolerance between the digital cut line and the mapped edges of the virtual 3D model of the fabricated dental aligner is determined. For example, in some embodiments, the comparator 322 may calculate a distance between the digital cut line and the edges to determine if the distance is within a threshold range (or value). In some embodiments, the comparator 322 may calculate an RMS value between the mapped edges in the virtual 3D model of the fabricated dental aligner and the digital cut line, and may determine if the RMS value is within a threshold range (or value). Accordingly, in some embodiments, the method 600 of FIG. 6 continues at operation 520 of FIG. 5, for example, to determine whether the comparisons result in the identification of any anomalous portions in the virtual 3D model of the fabricated dental aligner.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be X, Y, or Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The hardware and data processing components used to implement the various processes, operations, illustrative logics, logical blocks, modules, and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, flash memory, hard disk storage) for storing data and/or computer code for completing or facilitating the various processes, layers and circuits described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the systems and methods shown in the various exemplary embodiments are illustrative only. Additionally, any element disclosed in one embodiment may be incorporated or utilized with any other embodiment disclosed herein.

What is claimed is:

1. A method for analyzing a quality of a dental aligner, the method comprising:
    receiving, by a processor, a digital dental aligner generated based on a fabricated dental aligner, wherein the digital dental aligner is a point cloud of a virtual three-dimensional (3D) model of the fabricated dental aligner;
    analyzing, by the processor, the digital dental aligner to identify a quality characteristic of the fabricated dental aligner by comparing the virtual 3D model of the fabricated dental aligner with a point cloud of a 3D model of a dental arch of a corresponding patient, wherein the comparison comprises:
        identifying, by the processor, one or more common points on the point clouds of the 3D models;
        aligning, by the processor, the virtual 3D model of the fabricated dental aligner and the 3D model of the dental arch of the corresponding patient based on the one or more common points;
        calculating, by the processor, a distance between the one or more common points when the virtual 3D model of the fabricated dental aligner and the 3D model of the dental arch of the corresponding patient are aligned; and
        comparing, by the processor, the distance with a threshold; and
    flagging, by the processor, the fabricated dental aligner based on the identified quality characteristic, wherein the identified quality characteristic is based on the comparison of the distance with the threshold.

2. The method of claim 1, further comprising:
    comparing, by the processor, the digital dental aligner with a cut line file used to cut the fabricated dental aligner from a dental mold.

3. The method of claim 2, further comprising:
    determining, based on the comparison, whether the fabricated dental aligner was cut from the dental mold within a tolerance of an intended cut line.

4. The method of claim 2, wherein the comparison comprises:
    mapping, by the processor, at least a portion of a digital cut line to the digital dental aligner, the digital cut line based on the cut line file.

5. The method of claim 4, wherein the comparison comprises:
    determining, by the processor, whether the portion of the digital cut line corresponds to an edge of the digital dental aligner.

6. The method of claim 2, wherein the comparison comprises:
    overlaying, by the processor, a digital cut line from the cut line file with the digital dental aligner.

7. The method of claim 6, wherein the comparison comprises:
    calculating, by the processor, a distance between a portion of the digital cut line and an edge of the digital dental aligner.

8. The method of claim 1, wherein the digital dental aligner includes at least one of a two-dimensional image or a three-dimensional model of the fabricated dental aligner.

9. The method of claim 8, further comprising:
    comparing, by the processor, an image corresponding to the at least one of the two-dimensional image or the three-dimensional model of the fabricated dental aligner with a corresponding image of a dental mold used to form the fabricated dental aligner.

10. The method of claim 1, wherein surface features of the fabricated dental aligner are enhanced to capture the surface features when generating the digital dental aligner.

11. The method of claim 10, wherein the surface features are enhanced using a predetermined spectrum of light that illuminates the fabricated dental aligner to identify surface imperfections.

12. The method of claim 1, wherein flagging the fabricated dental aligner at least one of (i) causes a fabrication system to fabricate a replacement dental aligner, or (ii) indicates at least one of that the fabricated dental aligner requires further inspection by a technician or that the fabricated dental aligner is rejected.

13. The method of claim 1, further comprising:
    analyzing, by the processor, an image of a dental mold used to form the fabricated dental aligner to determine if the dental mold can be used to fabricate subsequent dental aligners.

14. A system for analyzing a quality of a dental aligner, the system comprising:
    a processor and memory coupled to the processor and storing instructions that, when executed by the processor, cause the processor to:
    receive a digital dental aligner generated based on a fabricated dental aligner, wherein the digital dental aligner is a point cloud of a virtual three-dimensional (3D) model of the fabricated dental aligner;
    analyze the digital dental aligner to identify a quality characteristic of the fabricated dental aligner by comparing the virtual 3D model of the fabricated dental aligner with a point cloud of a 3D model of a dental arch of a corresponding patient, wherein the comparison comprises:
  identifying one or more common points on the point clouds of the 3D models;
  aligning the virtual 3D model of the fabricated dental aligner and the 3D model of the dental arch of the corresponding patient based on the one or more common points;
  calculating a distance between the one or more common points when the virtual 3D model of the fabricated dental aligner and the 3D model of the dental arch of the corresponding patient are aligned; and
  comparing the distance with a threshold; and
flag the fabricated dental aligner based on the identified quality characteristic, wherein the identified quality characteristic is based on the comparison of the distance with the threshold.

15. The system of claim 14, wherein the instructions further cause the processor to:
  compare the digital dental aligner with a cut line file used to cut the fabricated dental aligner from a dental mold; and
  determine, from the comparison, whether the fabricated dental aligner was cut from the dental mold within a tolerance of an intended cut line.

16. The system of claim 15, wherein the instructions further cause the processor to:
  map at least a portion of a digital cut line to the digital dental aligner, the digital cut line based on the cut line file; and
  determine whether the portion of the digital cut line corresponds to a geometry of the fabricated dental aligner.

17. The system of claim 15, wherein the instructions further cause the processor to:
  overlay a digital cut line from the cut line file with the digital dental aligner; and
  calculate a distance between a portion of the digital cut line and a geometry of the digital dental aligner.

18. A quality control system comprising:
an imaging system configured to:
  enhance a quality characteristic of a fabricated dental aligner;
  capture an image of the quality characteristic; and
  generate a digital dental aligner including the quality characteristic of the fabricated dental aligner based on the captured image, wherein the digital dental aligner is a point cloud of a virtual three-dimensional (3D) model of the fabricated dental aligner; and
a processor and memory coupled to the processor and storing instructions that, when executed by the processor, cause the processor to:
  analyze the quality characteristic of the digital dental aligner by comparing the virtual 3D model of the fabricated dental aligner with a point cloud of a 3D model of a dental arch of a corresponding patient, wherein the comparison comprises:
    identifying one or more common points on the point clouds of the 3D models;
    aligning the virtual 3D model of the fabricated dental aligner and the 3D model of the dental arch of the corresponding patient based on the one or more common points;
    calculating a distance between the one or more common points when the virtual 3D model of the fabricated dental aligner and the 3D model of the dental arch of the corresponding patient are aligned; and
    comparing the distance with a threshold; and
  flag the fabricated dental aligner based on the analysis of the quality characteristic, wherein the identified quality characteristic is based on the comparison of the distance with the threshold.

19. The quality control system of claim 18, wherein flagging the fabricated dental aligner at least one of (i) causes a fabrication system to fabricate a replacement dental aligner, or (ii) indicates at least one of that the fabricated dental aligner requires further inspection by a technician or that the fabricated dental aligner is rejected.

* * * * *